(12) United States Patent
Umbarkar et al.

(10) Patent No.: US 11,111,207 B2
(45) Date of Patent: Sep. 7, 2021

(54) ONE POT, ONE STEP PROCESS FOR THE HALOGENATION OF AROMATICS USING SOLID ACID CATALYSTS

(71) Applicant: COUNCIL OF SCIENTIFIC AND INDUSTRIAL RESEARCH, New Delhi (IN)

(72) Inventors: Shubhangi Bhalchandra Umbarkar, Maharashtra (IN); Atul Balasaheb Kulal, Maharashtra (IN); Amar Jaywant Deshmukh, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/086,831

(22) PCT Filed: Mar. 17, 2017

(86) PCT No.: PCT/IN2017/050097
§ 371 (c)(1),
(2) Date: Sep. 20, 2018

(87) PCT Pub. No.: WO2017/163262
PCT Pub. Date: Sep. 28, 2017

(65) Prior Publication Data
US 2019/0100487 A1    Apr. 4, 2019

(30) Foreign Application Priority Data

Mar. 21, 2016 (IN) ............................. 201611009675

(51) Int. Cl.
| | | |
|---|---|---|
| *C07C 209/74* | (2006.01) | |
| *C07C 37/62* | (2006.01) | |
| *C07C 45/63* | (2006.01) | |
| *B01J 21/06* | (2006.01) | |
| *B01J 21/08* | (2006.01) | |
| *B01J 21/12* | (2006.01) | |
| *B01J 23/28* | (2006.01) | |
| *B01J 23/30* | (2006.01) | |
| *C07C 231/12* | (2006.01) | |
| *C07C 39/27* | (2006.01) | |
| *C07C 47/55* | (2006.01) | |
| *C07C 211/52* | (2006.01) | |
| *C07C 237/30* | (2006.01) | |

(52) U.S. Cl.
CPC ........... *C07C 209/74* (2013.01); *B01J 21/063* (2013.01); *B01J 21/08* (2013.01); *B01J 21/12* (2013.01); *B01J 23/28* (2013.01); *B01J 23/30* (2013.01); *C07C 37/62* (2013.01); *C07C 45/63* (2013.01); *C07C 231/12* (2013.01); *C07C 39/27* (2013.01); *C07C 47/55* (2013.01); *C07C 211/52* (2013.01); *C07C 237/30* (2013.01)

(58) Field of Classification Search
None
See application file for complete search history.

(56) References Cited

U.S. PATENT DOCUMENTS

| | | |
|---|---|---|
| 5,473,084 A | 12/1995 | Wang et al. |
| 6,124,512 A * | 9/2000 | Cook ....................... B01J 23/00 570/208 |
| 6,166,272 A | 12/2000 | Mandal |
| 6,225,514 B1 | 5/2001 | Cook et al. |

FOREIGN PATENT DOCUMENTS

GB        2155009 A        9/1985

OTHER PUBLICATIONS

International Search Report and Written Opinion, PCT/IN2017/050097, dated Jul. 17, 2017 (15 pp.).
Carniti, P., et al., Green Iodination of Phenol over Solid Acids, Catal Lett (2010) 137:55-62, DOI: 10.1007/s10562-010-0283-6 (8 pp.).
Hosseini, A., et al., Iodination of Activated Aromatic Compounds Using Nanostructure Solid Acid Catalyst, Synthetic Communications, 42:16, 2407-2424, DOI: 10.1080/00397911.2011.558967, 2011 (9 pp.).
Mallik, S., et al., Studies on heteropoly acid supported zirconia III: Oxidative bromination of phenol using phosphotungstic acid supported on zirconia, ScienceDirect, Journal of Molecular Catalysis A: Chemcial 261 (2007) 172-179 (8 pp.).
Saikia, L., et al., Regiospecific Oxyhalogenation of Aromatics Over SBA-15-Supported Nanoparticle Group IV-VI Metal Oxides, Catal Lett (2010) 137: 190-201, DOI: 10.1007/s10562-010-0350-z (12 pp.).
Comments to the International Search Report and Written Opinion, PCT/IN2017/050097, dated Sep. 13, 2017 (3 pp.).
Adimuthy, S., et al., A new, environment friendly protocol for iodination of electron-rich aromatic compounds, Tetrahedron Letters, vol. 44, Issue 27, pp. 5099-5101, Jun. 30, 2003 (3 pp.).

\* cited by examiner

*Primary Examiner* — Clinton A Brooks
(74) *Attorney, Agent, or Firm* — Eversheds Sutherland (US) LLP

(57) ABSTRACT

The present invention disclosed an improved one pot, one step process for halogenation of compound of formula (II) to afford corresponding halogenated compound of formula (I) having improved yield and increased selectivity under very mild conditions.

9 Claims, No Drawings

ONE POT, ONE STEP PROCESS FOR THE HALOGENATION OF AROMATICS USING SOLID ACID CATALYSTS

FIELD OF THE INVENTION

The present invention relates to halogenation of aromatics using solid acid catalysts. More particularly, the present invention relates to an improved one pot, one step process for the halogenation of compound of formula (II) to afford corresponding halogenated compound of formula (I) having improved yield and increased selectivity.

BACKGROUND AND PRIOR ART OF THE INVENTION

Halogenated hydrocarbons have many important industrial and technical uses which make these compounds extremely valuable, and which therefore make the possibility of producing such compounds in quantity and in an easily controllable, inexpensive manner extremely desirable. Halogenated aromatic hydrocarbons are particularly valuable as starting materials for many purposes, such as for the production of dyes, synthetic resins and insecticides. The functional halogen group of such compounds may be varied in many respects in order to give the obtained products a higher degree of color, a higher degree of flame-proofing, or even toxicity. The production of such halogenated aromatic compound is particularly difficult. The halogenation with elementary halogen usually results in a large loss of solvents, requires carefully controlled conditions, and thorough purification of the final product, one half of the utilized halogen is converted to the corresponding hydrogen halide compound and is thus lost for the halogenation.

Further, aryl iodides are important intermediates in organic synthesis, medicine and biochemistry. They are also valuable and reactive intermediates for various cross-coupling reactions, for example, Heck, Stille and Negishi cross-coupling. Direct iodination using $I_2$ is a simple method, but is not straight forward and requires the oxidation of iodine to the more reactive species with a pronounced $I^+$ nature. Iodination of aromatic compounds has been carried out using molecular iodine together with strong oxidizing agents such as nitric acid, sulphuric acid, iodic acid, sulphur trioxide and hydrogen peroxide, ceric ammonium nitrate, bismuth (III) nitrate pentahydrate, sodium hypochlorite and urea-hydrogen peroxide. Several reagents reported for iodination of aromatic compounds include iodine and 1,4-bis(triphenylphosphonium)-2-butene peroxodisulfate, iodine and pyridine/dioxane, $AgNO_3/I_2$, $I_2/NaBO_3.4H_2O$ in ionic liquid, $I_2/HIO_3$, heat, $I_2/CrO_3$, $NaClO_2/NaI/HCl$, $KI/K_2FeO_4$ in water, N-iodosuccinimide and catalytic trifluoroacetic acid, $pyCl/CH_3OH$, $I_2/Pb(OAc)_4$, $KI/H_2O_2$, $KI/KIO_3/H+$, $KClO_3/KI/HCl$, NCS/NaI and iodine with $H_2O_2$ and $O_2$. Strong Lewis acids or Bronsted acids, such as trifluoroacetic acid, trifluoromethanesulfonic acid and $BF_3.OEt_2-H_2O$ have been utilized for electron-withdrawing groups on the aromatic ring, which is not suitable for acid sensitive functional groups.

Hence, there is an increasing demand for new greener methods for iodination without catalyst and solvent. Iodination using ICl is usually carried out in polar solvents, such as methanol, water and acids such as acetic acid, trifluoroacetic acid, aq. hydrochloric acid, sulphuric acid, etc., in which the heterolytic dissociation facilitates electrophilic attack of iodine. Iodination using ICl is carried out in Lewis acids such as $Hg(OTf)_2$ and AgOTf. Very few ammonium $ICl_2$—salts have been reported for the iodination of aromatic compounds. Hexamethylene bis(Nmethylimidazolium) bis (dichloroiodate) an ionic liquid iodinating reagent has been used for iodination of aromatic amines. The drawback was that the reaction requires $CaCO_3$ as base and the recycle yields are less (82%). Benzyltrimethylammonium dichloroiodate was used for iodination. The drawback was the use of MeOH as solvent and the requirement of $CaCO_3$ as a base. A variety of 1,3-dialkylimidazolium trihalide-based ionic liquids were used for iodochlorination for alkenes and alkynes and not for iodination.

U.S. Pat. No. 6,225,514 disclosed a method of halogenating the ring of an aromatic compound. The aromatic compound is contacted with a halogenating agent in the presence of a heterogeneous catalyst. The catalysts of this invention, commonly known as "solid acid catalysts," can be made by reacting a dopant with a support. Examples of suitable dopants include $H_2SO_4$, $(NH_4)_2SO_4$, $(NH_4)HS\ O_4$, $SO_3$, $WO_3$, $H_2WO_4$, $H_2MoO_4$, $(NH_4)_2WO_4$, $(NH_4)_2MoO_4$, $Mo(NO_3)_6$, $W(NO_3)_6$, $MoO_3$, $H_3PO_4$, $(NH_4)_3PO_4$, $(NH_4)_2HPO_4$, $(NH_4)H_2PO_4$, $Cr_2O_3$, and mixtures thereof. Supports that can be used include $TiO_2$, $ZrO_2$, $HfO_2$, $MnO_2$, $Fe_2O_3$, $Fe_3O_4$, $GeO_2$, $SnO_2$, $TlO_3$, $Nb_2O_5$, $Ta_2O_5$, $SC_2O_3$, $La_2O_3$, $SiO_2$, and mixtures thereof.

Article titled "Regiospecific Oxyhalogenation of Aromatics Over SBA-15-Supported Nanoparticle Group IV-VI Metal Oxides" by L Saikia et al. published in *Catalysis Letters;* 2010, Volume 137, Issue 3, pp 190-201 reports Nanoparticulate $WO_x$, $MoO_x$, $TiO_x$ and $VO_x$ supported on SBA-15 for efficient catalytic activity for oxyhalogenation of aromatic compounds. The reaction occurs at 298 K and moderate acidic pH (3-5). The catalytic activity of these catalysts is higher than most of the hitherto known solid catalysts and unsupported metal oxides.

U.S. Pat. No. 6,166,272 disclosed a method of fluorinating a substrate comprising reacting said substrate with a fluorinating agent in the presence of about 0.01 to about 2 wt % molybdenum trioxide at a temperature between about 40 and about 100° C.

Article titled "Iodination of activated aromatic compounds using nanostructure solid acid catalyst" by A Hosseini et al. published in *Synthetic Communications,* 2012; 42; pp 2407-2414 reports iodination of aromatic compounds catalyzed by Nanoporous silica anchored with sulfonic acid groups. The reaction was performed in water using hydrogen peroxide as oxidant. The recyclability of catalyst in green media significantly contributes to the environmental friendliness of the procedure.

Article titled "Studies on heteropoly acid supported zirconia: III: Oxidative bromination of phenol using phosphotungstic acid supported on zirconia" by S Mallik et al. published in *Journal of Molecular Catalysis A: Chemical;* 2007, 261(2), pp 172-179 reports a series of ecofriendly solid acid catalyst synthesized by supporting phosphotungstic acid onto hydrous zirconia by an incipient wetness impregnation method in order to contribute towards clean technology. Further, Phosphotungstic acid supported on hydrous zirconia acts as an efficient and stable solid acid catalyst for oxybromination of phenol.

Article titled "A new, environment friendly protocol for iodination of electron-rich aromatic compounds" by S Adimurthy et al. published in *Tetrahedron Letters,* 2003, 44 (27), pp 5099-5101 reports a new environment friendly procedure for effective aromatic iodination. A mixture of potassium iodide and potassium iodate is used in the presence of an acid for in situ iodination of aromatic compounds.

Therefore, there is need to overcome prior art problems such as use of strong mineral acids, carried out at high temperature and high oxygen pressure, solvents are not environmental friendly and excess use of reagents and more importantly prior art fails to disclose the process for selectively obtaining ortho-halogenated compound. Accordingly, the present invention provides an environment friendly single pot process for halogenation of aromatic compounds under milder conditions with improved conversion and increased selectivity towards ortho substituted compounds using heterogeneous solid acid catalysts.

OBJECTIVE OF THE INVENTION

The main objective of the present invention is to provide an improved one pot, one step process for the halogenation of compound of formula (II) to afford corresponding halogenated compound of formula (I) having improved yield and increased selectivity.

Another objective of the present invention is to provide an improved one pot, one step process for iodination of aromatics of compound of formula (II) to corresponding iodo compound of formula (I) in presence of suitable catalyst using $I_2$ having improved yield and increased selectivity.

Yet another objective of the present invention is to provide an improved one pot, one step process for the halogenation of aminoaromatic or hydroxy aromatic or aromatic aldehyde compound using suitable halogenating agent and solid acid catalyst to afford corresponding halogenated compound having improved yield and increased selectivity.

SUMMARY OF THE INVENTION

Accordingly, the present invention provides an improved one pot, one step process for the halogenation of substituted aromatic compound comprises addition of halogenating agent and solid acid catalyst to the mixture of substituted aromatic compound in solvent followed by stirring the reaction mixture at temperature in the range of 25 to 150° C. for the period in the range of 2 to 6 hrs to afford corresponding halogenated compound.

In preferred embodiment, said substituted aromatic compound is selected from aminoaromatic compound, hydroxy aromatic compound, aromatic aldehyde compound, halo substituted aromatics, amide substituted aromatic compound.

In another preferred embodiment, said aminoaromatic compound is selected from aniline, 4-Chloroaniline, 4-Bromoaniline, 2,6 dimethyl aniline, anthranilamide, 2,6 diethyl aniline.

In yet another preferred embodiment, wherein said hydroxy aromatic compound is selected from phenol.

In still another preferred embodiment, said aromatic aldehyde compound is benzaldehyde.

In yet still another preferred embodiment, said corresponding ortho-halogenated compound is selected from 4-chloro-2-iodoaniline, 2-iodoaniline, 4-bromo-2-iodoaniline, 4-iodo-2,6-dimethylaniline, 3-iodobenzaldehyde, 2-iodophenol, 2-amino-3-iodobenzamide, 2,6-diethyl-4-iodoaniline, 4-chloro-2,6-dimethylaniline and 4-bromo-2,6-dimethylaniline.

In yet still another preferred embodiment, said solid acid catalyst is selected from $SiO_2$, $MoO_3/TiO_2$, $MoO_3/TiO_2$, $WO_3/TiO_2$, $WO_3/TiO_2$ and 5% Mo Si/Al (7.5) Impr.

In yet still another preferred embodiment, said solvent is selected from ethylene dichloride, methanol, hexane, toluene, dichloromethane, ethanol, higher alcohols, dimethyl sulfoxide, dioxane, dimethylformamide, acetone, diethyl ether, butanol and benzylalcohol.

In yet still another preferred embodiment, selectivity towards said corresponding ortho-halogenated aromatic compound is in the range of 50 to 100%.

In yet still another preferred embodiment, said process is carried out in batch mode or continuous mode.

DETAILED DESCRIPTION OF THE INVENTION

The invention will now be described in detail in connection with certain preferred and optional embodiments, so that various aspects thereof may be more fully understood and appreciated.

In the view of above, the present invention provides an improved one pot, one step process for the halogenation of compound of formula (II);

Formula (II)

Wherein;
R1 is selected from alkyl, amines, carbonyl containing compounds, halides, amides and acids;
R2 and R3 is selected from the hydrogen, halogen, alkyl, aryl and amine; to afford corresponding halo compound of formula (I)

Formula (I)

Wherein;
X is selected from chlorine, bromine, iodine;
R1 is selected from alkyl, amines, carbonyl containing compounds, halides, amides and acids;
R2 and R3 is selected from the hydrogen, halogen, alkyl, aryl and having improved yield and increased selectivity.

In an embodiment, the present invention provides an improved one pot, one step process for iodination of aromatics of compound of formula (II) to corresponding iodo compound of formula (I) in presence of suitable catalyst and solvent using $I_2$ as iodinating agent having improved yield and increased selectivity.

In another embodiment, the present invention provides an improved one pot, one step process for the halogenation of substituted aromatic compound comprises addition of halogenating agent and solid acid catalyst to the mixture of substituted aromatic compound in solvent followed by stirring the reaction mixture at temperature in the range of 25 to 150° C. for the period in the range of 2 to 6 hrs to afford corresponding halogenated compound.

In preferred embodiment, said substituted aromatic compound is selected from aminoaromatic compound, hydroxy aromatic compound, aromatic aldehyde compound, halo substituted aromatics, amide substituted aromatic compound.

In another preferred embodiment, said aminoaromatic compound is selected from aniline, 4-Chloroaniline, 4-Bromoaniline, 2,6 dimethyl aniline, anthranilamide, 2,6 diethyl aniline.

In yet another preferred embodiment, wherein said hydroxy aromatic compound is selected from phenol.

In still another preferred embodiment, said aromatic aldehyde compound is benzaldehyde.

In yet still another preferred embodiment, said corresponding ortho-halogenated compound is selected from 4-chloro-2-iodoaniline, 2-iodoaniline, 4-bromo-2-iodoaniline, 4-iodo-2,6-dimethylaniline, 3-iodobenzaldehyde, 2-iodophenol, 2-amino-3-iodobenzamide, 2,6-diethyl-4-iodoaniline, 4-chloro-2,6-dimethylaniline and 4-bromo-2,6-dimethylaniline.

In yet still another preferred embodiment, said solid acid catalyst is selected from $SiO_2$, $MoO_3/TiO_2$, $MoO_3/TiO_2$, $WO_3/TiO_2$, $WO_3/TiO_2$ and 5% Mo Si/Al (7.5) Impr.

In yet still another preferred embodiment, said solvent is selected from ethylene dichloride, methanol, hexane, toluene, dichloromethane, ethanol, higher alcohols, dimethylsulfoxide, dioxane, dimethylformamide, acetone, diethyl ether, butanol and benzylalcohol.

In yet still another preferred embodiment, selectivity towards said corresponding ortho-halogenated aromatic compound is in the range of 50 to 100%.

In yet still another preferred embodiment, said process is carried out in batch mode or continuous mode.

The halogenation is carried out in batch mode.

The halogenation is carried out in continuous mode in down-flow reactor.

The improved one pot, one step process for the halogenation of compound of formula (II) is to afford corresponding halo compound of formula (I) is depicted in scheme 1 below:

Scheme 1

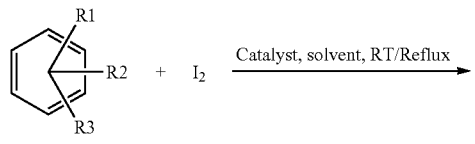

Formula (II)

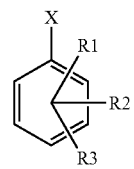

Formula (I)

A range of heterogeneous solid acid catalysts are used for iodination of aromatics to corresponding iodo compounds with up to 97% conversion and 100% selectivity using $I_2$ as iodinating agent and ethylene dichloride as solvent at only 80° C.

The following examples, which include preferred embodiments, will serve to illustrate the practice of this invention, it being understood that the particulars shown are by way of example and for purpose of illustrative discussion of preferred embodiments of the invention.

EXAMPLES

Following examples are given by way of illustration and therefore should not be construed to limit the scope of the invention.

Example: 1 General Procedure for the Synthesis of Halo Compound of Formula I

A 25 mL two-necked round bottom flask was fitted with condenser. Initially 0.1 g substrate (0.001 mol) was added to the flask followed by 10 mL solvent. After this 0.28 g iodine (0.001 mol) was added to the same flask followed by addition of 0.02 g catalyst. The reaction was carried out at different temperatures (Table 1) for 2-6 hrs. After completion of the reaction, 5 mL water was added to the reaction flask to stop the reaction. The reaction was monitored by GC analysis.

The compounds which are used for the iodination of aromatics are listed in table 1 below:

TABLE 1

Liquid phase iodination of aromatics

| Ex no. | Substrate | Catalyst | Temp, ° C. | Molar ratio of Sub:$I_2$ | Solvent | % Catalyst loading wrt substrate | % Conv. | % Selectivity | |
|---|---|---|---|---|---|---|---|---|---|
| 1 | 4-Chloroaniline (NH₂, Cl) | $SiO_2$ | 28° C. | 1:0.5 | Hexane | 10 | 45 | 4-chloro-2-iodoaniline 94 | 4-chloro-3-iodoaniline 6 |

TABLE 1-continued

Liquid phase iodination of aromatics

| Ex no. | Substrate | Catalyst | Temp, °C. | Molar ratio of Sub:I₂ | Solvent | % Catalyst loading wrt substrate | % Conv. | % Selectivity | | |
|---|---|---|---|---|---|---|---|---|---|---|
| 2 | 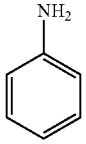 Aniline | 20% MoO₃/ TiO₂ | 65° C. | 1:1 | MeOH | 5 | 91 | 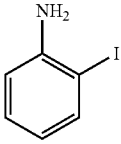 2-iodoaniline 92 | 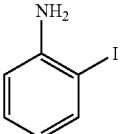 2,4-diiodoaniline 8 | |
| 3 | 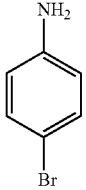 4-Bromoaniline | 2% WO₃/ TiO₂ | 68° C. | 1:0.5 | Hexane | 20 | 48 | 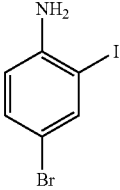 4-bromo-2-iodoaniline 58 | 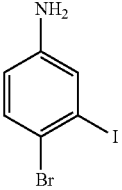 4-bromo-3-iodoaniline 20 | #OP 22 |
| 4 | 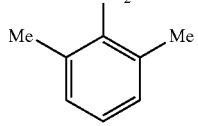 2,6 dimethyl aniline | 20 wt % WO₃/ SiO₂ | 28° C. | 1:1.2 | EDC | 10 | 85 | 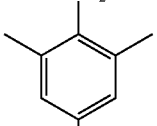 4-iodo-2,6-dimethylaniline 100 | | |
| 5 | 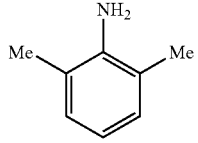 2,6 dimethyl aniline | 20 mol % MoO₃/ SiO₂ | 28° C. | 1:1.2 | EDC | 10 | 65 | 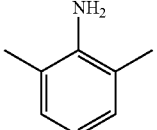 4-iodo-2,6-dimethylaniline 100 | | |
| 7 | 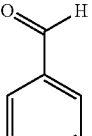 Benzaldehyde | 5% MoSi/ Al (7.5) Impr | 40° C. | 1:1.2 | EDC | 5 | 3 | 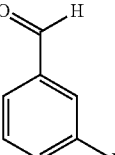 3-iodobenzaldehyde 100 | | |

TABLE 1-continued

Liquid phase iodination of aromatics

| Ex no. | Substrate | Catalyst | Temp, °C. | Molar ratio of Sub:I$_2$ | Solvent | % Catalyst loading wrt substrate | % Conv. | % Selectivity | |
|---|---|---|---|---|---|---|---|---|---|
| 8 | Phenol | 20 wt % WO$_3$/SiO$_2$ | 28° C. | 1:1.2 | MeOH | 20 | 11 | 2-iodophenyl 90 | 4-iodophenol 10 |
| 9 | Phenol | 20 wt % WO$_3$/SiO$_2$ | 65° C. | 1:1.2 | MeOH | 20 | 22 | 2-iodophenyl 90 | 4-iodophenol 10 |
| 10 | Anthranilamide | 20 wt % MO$_3$/SiO$_2$ | 84° C. | 1:1.2 | EDC | 20 | 88 | 2-amino-3-iodobenzamide 55 | 2-amino-5-iodobenzamide 30 [#OP 15] |
| 11 | 2,6 dimethyl aniline | 20 wt % MO$_3$/SiO$_2$ | 84° C. | 1:1.2 | EDC | 20 | 88 | 2,6-diethyl-4-iodoaniline 98 | 3-iodo-2,6-dimethylaniline 2 |

OP = Other products

Example 2: Catalyst Preparation a) SiO$_2$:

In a typical procedure, SiO$_2$ catalyst was synthesized by dissolving ES-40 (50.0 g) in IPA (35 mL) with constant stirring. To this solution 3 mL dil. NH$_4$OH (2.5%) solution was added. The solution was stirred until white gel was obtained. The resultant gel was air dried and further calcined at 500° C. in air in a muffle furnace for 5 h.

b) 20% WO$_3$/SiO$_2$:

In a typical procedure, 20 WS catalyst was synthesized by dissolving 5.31 g AMT in 10 mL distilled water. This solution was added drop wise to the dry IPA solution (35 mL) of ES-40 (50.0 g) with constant stirring. To this solution 3 mL dil. NH$_4$OH (2.5%) solution was added. The solution was stirred until white gel was obtained. The resultant gel was air dried and further calcined at 500° C. in air in a muffle furnace for 5 h. Similarly catalysts with 1, 5, 10, 15, 25 and 30 wt % tungsten oxide loadings were prepared.

c) 20 mol % MoO$_3$/SiO$_2$:

In a typical procedure, 20 m % MoO$_3$/SiO$_2$ catalyst was synthesized by dissolving 14.11 g of ABM in 40 ml of water at 80° C. This hot solution was added dropwise to a dry isopropyl alcohol solution of ethyl silicate-40 (48.0 g) with constant stirring. The resultant transparent greenish gel was air-dried and calcined at 500° C. in air in a muffle furnace for 12 h. Similarly, catalysts with 1, 10 and 30 mol % molybdenum oxide loading were prepared.

d) 20% $MoO_3/TiO_2$:

In typical procedure Titanium(IV) tetrabutoxide hydrolysed with deionized water (500 mL) and stirred vigorously for 10 min. The resulting titanium hydroxide precipitate separated by decantation and thoroughly washed with water until the alcohol generated during the hydrolysis of titanium alkoxide completely removes. Then precipitate dissolved in aqueous hydrogen peroxide (50%), which resulted in a very exothermic reaction. Additional water (200 mL) added to reduce the reaction rate and avoid the development of a highly viscous polymeric gel phase. A clear yellow solution formed within 30 min, the colour of which is characteristic of a titanium peroxo complex. To it added the aqueous solution of precursor $MoO_3$ dropwise with stirring. Then the solution was kept overnight to form the uniform gel. After gelation air dried the gel, crushed it. The resulting powder dried in oven @ 100° C. then calcined @ 500° C. for 5 hr. (heating rate 2° C./min.).

e) 2% $WO_3/TiO_2$:

In typical procedure Titanium(IV) tetrabutoxide hydrolysed with deionized water (500 mL) and stirred vigorously for 10 min. The resulting titanium hydroxide precipitate separated by decantation and thoroughly washed with water until the alcohol generated during the hydrolysis of titanium alkoxide completely removes. Then precipitate dissolved in aqueous hydrogen peroxide (50%), which resulted in a very exothermic reaction. Additional water (200 mL) added to reduce the reaction rate and avoid the development of a highly viscous polymeric gel phase. A clear yellow solution formed within 30 min, the colour of which is characteristic of a titanium peroxo complex. To it added the aqueous solution (in 50% $H_2O_2$) of precursor AMT dropwise with stirring. Then the solution was kept overnight to form the uniform gel. After gelation air dried the gel, crushed it. The resulting powder dried in oven @ 100° C. then calcined @ 500° C. for 5 hr. (heating rate 2° C./min.).

f) 5% Mo Si/Al (7.5) Impr:

In typical procedure aluminium isopropoxide was taken in a beaker to this IPA was added, kept for stirring. To dissolve aluminium isopropoxide $HNO_3$ was added ml by ml till it dissolves. In a separate beaker TEOS+IPA was taken, kept for stirring. To the clear solution of aluminium isopropoxide, TEOS+IPA mixture was added drop wise with stirring. The homogeneous mixture was stirred for 2 hrs then $NH_3$ (1% $NH_3$ in IPA) was added drop wise for gelation. The viscous liquid kept for gelation. Formed gel was oven dried at 60° C. The dried, grinded gel kept for calcination for 5 hr at 500° C. Then aqueous solution of ammonium heptamolybdate added to silica alumina support in an impregnation method. This mixture was stirred on hot plate to dry with stirring. The dried catalyst was calcined at 500° C. for 5 hr.

Example 3: Recycle Study for Liquid Phase Iodination of Aromatics

A 250 mL two-necked round bottom flask fitted with condenser was charged 1 g 2,6 Dimethyl aniline (0.01 mol), 2.5 g iodine (0.01 mol), 100 mL 1,2-dichloroethane, and 0.2 g catalyst. The flask was flushed with argon. The reaction was carried out at room temperature (Table 2) for 1 hr. The reaction was monitored by GC analysis. The reaction mixture decanted leaving catalyst in the RB. The RB was charged with fresh reactants and it was stirred for 1 hr. The cycle was repeated 3 times.

TABLE 2

Recycle study

| Sr. No. | Recycle no. | % conversion |
|---|---|---|
| 1 | 0 | 77 |
| 2 | 1 | 74 |
| 3 | 2 | 78 |
| 4 | 3 | 76 |

Example 4: Continuous Flow Iodination

In 10 cm fixed bed reactor 2 g 20% $WO_3/SiO_2$ was loaded. Reaction mixture containing 1 g aniline (0.01 mol), 2.8 g Iodine (0.01 mol) dissolved in 50 mL ethylene dichloride passed through the reactor at the flow rate of 3.5 ml/hr. Samples were collected at regular intervals and analyzed with GC. (Table 3)

TABLE 3

Continuous flow iodination

| Sr. No. | Sample (hrs) | % conversion |
|---|---|---|
| 1 | 0.25 | 69 |
| 2 | 0.5 | 68 |
| 3 | 0.75 | 68 |
| 4 | 1 | 70 |
| 5 | 3.5 | 69 |
| 6 | 7 | 68 |
| 7 | 18 | 70 |

Example 5: Bromination of Aniline

A 25 mL two-necked round bottom flask was fitted with condenser. Initially 0.1 g aniline (0.001 mol) was added to the flask followed by 10 mL solvent. After this 0.1 g bromine (0.0012 mol) was added to the same flask followed by addition of 0.02 g 20% $WO_3/SiO_2$ catalyst. The reaction was carried out at room temperature (25° C.) for 10 mins. The reaction was monitored by GC analysis. There was 100% aniline conversion observed with 40, 50 and 10% selectivity for 2-bromo aniline, 4-bromo aniline and 2,4-dibromo aniline respectively.

Example 6: Chlorination of Aniline

A 25 mL two-necked round bottom flask was fitted with condenser. Initially 0.1 g aniline (0.001 mol) was added to the flask followed by 10 mL solvent. After this 0.02 g of catalyst 20% $WO_3/SiO_2$ added. Later 0.027 g of chlorine (0.001 mol) gas was passed through the reaction flask. The reaction was carried out at room temperature (25° C.) for 10 mins. The reaction was monitored by GC analysis. There was 40% aniline conversion observed with 40 and 60% selectivity for 2-chloro aniline and 4-chloro aniline respectively.

Example 7: Chlorination of Aniline

A 25 mL two-necked round bottom flask was fitted with condenser. Initially 0.1 g aniline (0.001 mol) was added to the flask followed by 10 mL solvent. After this 0.02 g of catalyst 20% WO$_3$/SiO$_2$ added. Later 0.04 g of chlorine (0.0015 mol) gas was passed through the reaction flask. The reaction was carried out at room temperature (25° C.) for 60 mins. The reaction was monitored by GC analysis. There was 100% aniline conversion observed with 40 and 60% selectivity for 4-chloro aniline and 2,4-dichloro aniline respectively.

ADVANTAGES OF THE INVENTION

1. Halogenation of anilines can be carried out with >90% conversion in only 30 mins.
2. Very mild reaction conditions, No harmful or hazardous reagents needed for the reaction.
3. Ease of catalyst handling due to heterogeneous catalyst working at mild reaction conditions, Catalysts could be recycled very easily by just filtration or decantation.
4. No decrease in the conversion as well as selectivity in recycle runs.
5. No need to regenerate the catalyst or activate the catalyst for next cycles.
6. The iodination carried out in continuous mode in downflow reactor at room temperature (at 25-28° C.).

The invention claimed is:

1. An improved one pot, one step process for the halogenation of substituted aromatic compound selected from hydroxy aromatic compound, aromatic aldehyde compound, halo substituted aromatics, amide substituted aromatic compound and amino aromatic compound, said process consists of:
addition of halogenating agent selected from chlorine, bromine or iodine and solid acid catalyst to the mixture of substituted aromatic compound in solvent selected from ethylene dichloride, methanol, hexane, toluene, ethanol, higher alcohols, dimethylsulfoxide, dioxane, dimethylformamide, acetone, diethyl ether, butanol and benzylalcohol followed by stirring the reaction mixture at temperature in the range of 25 to 85° C. and at atmospheric pressure of 14 psig for the period in the range of 2 to 6 hrs to afford corresponding halogenated compound wherein said solid acid catalyst is selected from MoO$_3$/TiO$_2$, MoO$_3$/SiO$_2$, WO$_3$/TiO$_2$, WO$_3$/SiO$_2$, and Mo Si/Al (7.5);
wherein no mixed halogenated products are produced;
wherein said catalyst is recyclable.

2. The process as claimed in claim 1, wherein said aminoaromatic compound is selected from aniline, 4-Chloroaniline, 4-Bromoaniline, 2,6 dimethyl aniline, anthranilamide, 2,6 diethyl aniline.

3. The process as claimed in claim 1, wherein said hydroxy aromatic compound is selected from phenol.

4. The process as claimed in claim 1, wherein said aromatic aldehyde compound benzaldehyde.

5. The process as claimed in claim 1, wherein said corresponding halogenated compound is selected from 4-chloro-2-iodoaniline, 2-iodoaniline, 4-bromo-2-iodoaniline, 4-iodo-2,6-dimethylaniline, 3-iodobenzaldehyde, 2-iodophenol, 2-amino-3-iodobenzamide, 2,6-diethyl-4-iodoaniline, 4-chloro-2,6-dimethylaniline and 4-bromo-2,6-dimethylaniline.

6. The process as claimed in claim 1, wherein selectivity towards corresponding ortho-halogenated compound is in the range of 50 to 100%.

7. The process as claimed in claim 1, wherein said process is carried out in batch mode or continuous mode.

8. The process as claimed in claim 1, wherein aniline conversion to bromination is 100% and selectivity for 2-bromo aniline, 4-bromo aniline and 2,4-dibromo aniline is 40%, 50% and 10% respectively.

9. The process as claimed in claim 1, wherein aniline conversion to chlorination is 100% and selectivity for 4-chloro aniline and 2,4-dichloro aniline is 40% and 60% respectively.

\* \* \* \* \*